United States Patent [19]

LaPetina et al.

[11] Patent Number: 4,830,774

[45] Date of Patent: May 16, 1989

[54] ANTIDANDRUFF SHAMPOO COMPOSITION HAVING IMPROVED SUSPENSION PROPERTIES

[75] Inventors: Donna M. LaPetina, Oakbrook Terrace; Chaitanya Patel, Hanover Park, both of Ill.

[73] Assignee: Helene Curtis, Inc., Chicago, Ill.

[21] Appl. No.: 132,727

[22] Filed: Dec. 11, 1987

Related U.S. Application Data

[63] Continuation of Ser. No. 874,542, Jun. 16, 1986, abandoned.

[51] Int. Cl.[4] ........................... C11D 3/32; C11D 3/37
[52] U.S. Cl. .................. 252/174.24; 252/106; 252/155; 252/174.23; 252/315.4; 252/544; 252/DIG. 13; 424/70; 514/852; 514/885
[58] Field of Search ............... 252/106, 154, 155, 173, 252/550, 559, 174.23, 174.25, 544, 174.24, DIG. 13; 424/70; 514/852, 885

[56] References Cited

U.S. PATENT DOCUMENTS

| 3,964,500 | 6/1976 | Drakoff | 252/550 |
| 4,235,898 | 11/1980 | Watanabe et al. | 252/154 |
| 4,452,732 | 6/1984 | Bolich, Jr. | 252/117 |
| 4,576,744 | 3/1986 | Edwards et al. | 252/554 |

Primary Examiner—A. Lionel Clingman
Assistant Examiner—Hoa Van Le
Attorney, Agent, or Firm—Mason, Kolehmainen, Rathburn & Wyss

[57] ABSTRACT

An antidandruff shampoo composition includes a suspension composition for particulate matter to achieve an unexpected reduction in shampoo separation while maintaining acceptable shampoo viscosities and foaming levels. The suspension composition includes a suspending alkanolamide and/or a wax ester in conjunction with an ethylene-maleic anhydride resin or a polyacrylic acid resin to yield anionic surfactant-based antidandruff shampoos of improved stability and aesthetics.

47 Claims, 7 Drawing Sheets

SEPARATION STUDIES

ANTIDANDRUFF SHAMPOO COMPOSITION HAVING IMPROVED SUSPENSION PROPERTIES CROSS REFERENCE TO RELATED APPLICATION

This application is a continuation of application Ser. No. 874,542, filed June 16, 1986, now abandoned.

FIELD OF THE INVENTION

The present invention relates to an antidandruff hair shampoo composition including a suspension composition capable of achieving a substantial and unexpected reduction in separation of solid, particulate matter, particularly a solid antidandruff agent, while maintaining acceptable shampoo viscosities and foaming levels. More particularly, the present invention is directed to an antidandruff shampoo composition containing discrete suspended, solid antidandruff agent particles, such as zinc pyrithione or sulfur, and to a suspension composition for the antidandruff shampoo including a suspending alkanolamide and/or a wax ester in conjunction with an ethylenemaleic anhydride resin or a polyacrylic acid resin. The suspension composition, present at a low level of about 3% maximum, imparts improved antidandruff agent suspension over a wide range of viscosities.

BACKGROUND OF THE INVENTION

The incorporation of antidandruff agents into anionic surfactant-based hair shampoos is well known. The individual antidandruff agents must not only relieve the flaking and itching symptoms of dandruff, but also be substantive to the skin and hair in order to extend the antidandruff agent's efficacy from one treatment to the next. These properties are most often found in compounds not soluble in aqueous media, and this inherent insolubility of the antidandruff agents makes formulation of a stable, aqueous, anionic surfactant-based antidandruff shampoo a difficult problem.

In order to incorporate such effective, sparsely soluble antidandruff agents as zinc pyrithione or sulfur into aqueous anionic surfacant-based hair shampoos, one or more suspending agents are required to keep the antidandruff agent homogeneously dispersed throughout the aqueous solution. Failure to adequately suspend the antidandruff agent leads to eventual shampoo separation as the antidandruff agent settles to the bottom of the container, and results in poor dandruff control and consumer complaints. Early antidandruff shampoo compositions used bentonite clay as the suspending agent, however, the trend has been to avoid bentonite since it gives the shampoo a dirty appearance and dries the hair due to the substantial oil absorption characteristic of bentonite. As a result, there has been a continuous search for suitable suspending agents capable of effectively dispersing antidandruff agents such as zinc pyrithione or sulfur.

In general, compositions containing insoluble particulate matter require a suspending agent to assist in dispersing the particulate matter evenly throughout the composition. Depending upon the ultimate use of the composition, the suspending agent may be any one of a number of inorganic minerals or synthetic or natural polymers or gums. Among the most often used suspension agents are colloidal aluminum oxide, modified magnesium aluminum silicate, xanthan gum, fumed silica, algin products, polyacrylic acid, sodium carboxymethylcellulose, hydroxypropylcellulose, synthetic sodium magnesium silicate, colloidal attapulgite clay, lignins and alkanolamides. In most compositions, the addition of a suspending agent at a great enough percentage to adequately suspend the particles in solution leads to an increase in viscosity.

Common hair shampoos are known to contain an effective low-to-non-irritating amount of an anionic surfactant, usually an alkyl sulfate, as a principal cleansing agent. Hair shampoos also include other components to improve product efficacy, stability and consumer acceptance. Therefore, any antidandruff agent and additional suspending agents added to a basic hair shampoo is expected to add antidandruff properties to the shampoo without detracting from the cleaning efficiency and aesthetic appeal of the shampoo. Unfortunately, the antidandruff agents and necessary suspending agents often adversely affect the foaming characteristics of the shampoo composition. Consumers perceive a substantial benefit in copious suds formation, since they incorrectly equate copious foam with excellent cleaning, and poor sudsing with inferior shampoos. The decreasing foaming capability of the antidandruff shampoos may be overcome by increasing the surfactant level of the shampoo, however, this option usually is avoided due to economic factors and oil extraction from the hair by detergent overformation.

Consumer acceptance of antidandruff hair shampoos also is influenced by the viscosity of the shampoo. The ideal shampoo should be thick enough to appear concentrated and not too run out of the container or hand to easily during application, and be thin enough for easy dispensing from the container, ease of application to the hair and even distribution over the scalp. These characteristics usually are found in a viscosity range from about 2000 cps to about 8000 cps. Some antidandruff suspending agent compositions tend to increase the viscosity of the shampoo outside consumer acceptable limits.

The Winkler U.S. Pat. No. 4,470,982, discloses a suspending agent composition for antidandruff agents including about 4% to about 6% of either the ethylene glycol esters of fatty acids having from about 16 to about 22 carbon atoms; alkanolamides of fatty acids having from about 16 to about 22 carbon atoms; or alkyl ($C_{16}$—$C_{22}$) dimethyl amine oxides to produce antidandruff shampoo compositions of good viscosity and acceptably low separation. In accordance with the Winkler patent, the levels of suspending agent, surfactant and alkanolamide are critical to the utility of the shampoo compositions.

In accordance with the present invention, anionic surfactant-based antidandruff shampoo compositions show substantial and unexpected reduction in shampoo separation, while maintaining acceptable shampoo viscosities and foaming levels, by including a suspending agent composition comprising a suspending alkanolamide and/or a wax ester in conjunction with an ethylene-maleic anhydride resin or polyacrylic acid resin. The suspending agent composition is incorporated into the antidandruff shampoo composition at a low levels of about 1% to about 3% by weight of the shampoo composition, thereby minimizing or avoiding any deterioration of foaming characteristics or viscosity of the shampoo.

SUMMARY OF THE INVENTION

In brief, it has been found that the addition of an ethylene-maleic anhydride (EMA) resin or a polyacrylic acid resin to an anionic surfactant-based antidandruff hair composition significantly and unexpectedly improves the particulate suspension properties of alkanolamides and/or wax ester suspending agents of the shampoo composition. The combination of the ethylene-maleic anhydride resin or polyacrylic acid resin with the alkanolamide and/or wax ester provides an antidandruff shampoo composition unexpectedly resistant to composition separation, and of a suitable viscosity, by utilizing relatively low levels, generally less than about 4.0%, of suspending agents. Also, using low levels of suspending agents minimizes the anti-foaming properties of the antidandruff shampoo.

Therefore, it is an object of the present invention to provide an antidandruff shampoo capable of effectively cleaning hair and imparting antidandruff properties to the hair in a single shampooing.

It is also an object of the present invention to provide an antidandruff shampoo composition, containing insoluble particulate matter and exhibiting minimal separation, while retaining suitable viscosities and foaming properties.

Another object of the present invention is to provide a suspending agent composition capable of homogeneously suspending insoluble particulate matter throughout an antidandruff shampoo composition for extended periods with minimal anti-foaming tendencies over a desired viscosity range.

Another object of the present invention is to provide an antidandruff shampoo composition having acceptable shampoo separation, viscosity and foaming characteristics while containing an unexpectedly low percentage of suspending agents.

Another object of the present invention is to provide an anionic surfactant-based antidandruff shampoo containing an alkanolamide and/or a wax ester, together with a neutralized carboxylic acid-containing resin, as the suspending agent composition for one or more insoluble antidandruff agents.

Another object of the present invention is to provide an alkyl sulfate-based shampoo, containing a particulate antidandruff agent suspended in a liquid carrier by a suspending agent composition comprising (1) an alkanolamide and/or wax ester, and (2) a neutralized ethylene-maleic anhydride resin and/or neutralized polyacrylic acid resin.

The above and other objects and advantages of the present invention will become apparent from the following detailed description of the invention taken in conjunction with the drawings.

DETAILED DESCRIPTION OF THE PREFERRED EMBODIMENTS

Figure 1:
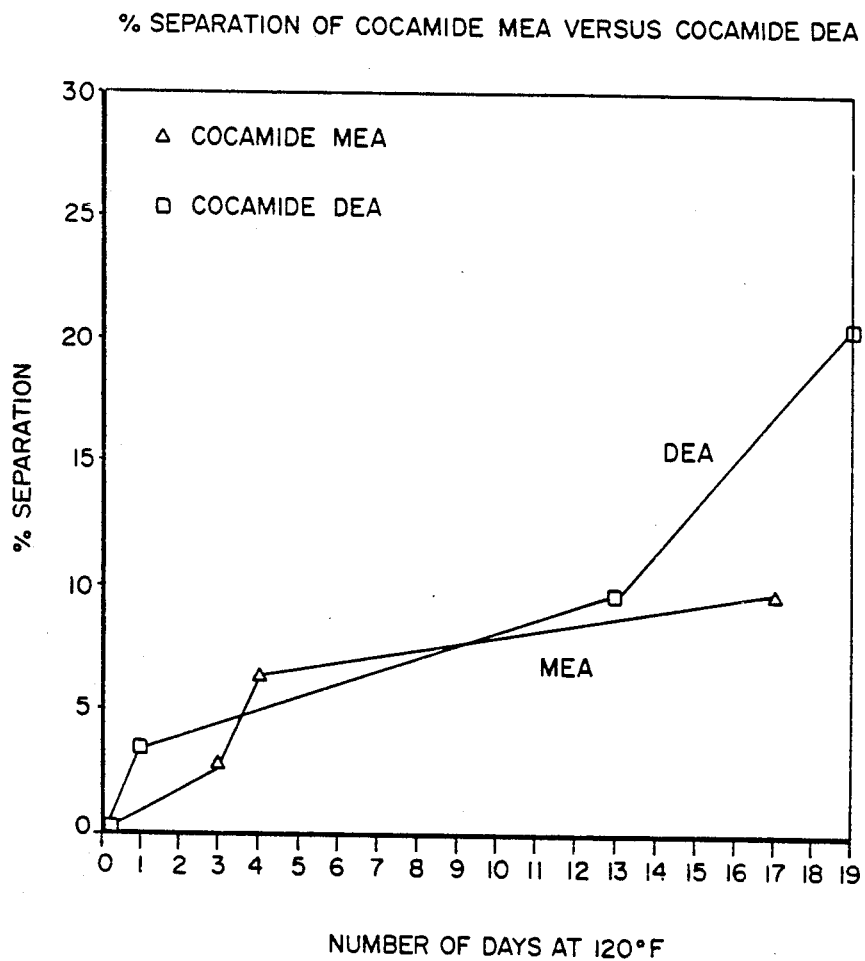
FIG. 1 is a graph comparing the ability of coconut monoethanolamide and coconut diethanolamide to suspend an antidandruff agent in the hair shampoo composition of Winkler U.S. Pat.No. 4,470,982.

The antidandruff hair shampoo compositions of the present invention are liquid anionic surfactant-based shampoos containing an insoluble antidandruff agent homogeneously dispersed and suspended throughout the composition. The antidandruff shampoo composition serves to cleanse the hair and relieve the itching and flaking symptoms of dandruff, while retaining the essential commercial qualities of suitable viscosity and copious foam.

The antidandruff agents of the present invention are any particulate compound capable of relieving the symptoms of dandruff and that are substantive to the hair and scalp to afford residual antidandruff properties between shampoos. Among the many particulate compounds exhibiting antidandruff properties are salicylic acid, elemental sulfur, selenium dioxide, zinc pyrithione, other 1-hydroxy pyridones and the azole antimycotics. Particularly advantageous antidandruff agents useful in the shampoo composition of the present invention are zinc pyrithione and elemental sulfur. Zinc pyrithione is the zinc complex of 2-pyridinethiol-1-oxide, and is available commercially from Olin Corp. under the brand name of ZINC OMADINE. Useful sulfurs include elemental sulfur of sufficient purity and particle size to function as an antidandruff agent, as well known in the art.

The antidandruff agents are extremely insoluble and, therefore, are present in the antidandruff shampoo composition as discrete solid particles. These particles should be homogeneously dispersed and suspended throughout the shampoo to ensure the consumer of an efficacious dose of antidandruff agent at each shampooing. Without a suspending agent composition, the antidandruff agent may completely separate from the hair shampoo composition resulting in poor dandruff control, and ultimately in consumer dissatisfaction and complaints. Therefore, a suspending agent composition must be incorporated into the basic antidandruff formulation to retard, minimize or eliminate settling of the insoluble antidandruff agent.

The antidandruff agent is present in the shampoo in a topically effective amount, generally between about 0.25% and about 5% by total weight of the shampoo. These limits are well above the solubility limits of the antidandruff agents in water (e.g., zinc pyrithione is 0.0015% by weight soluble in water), and, therefore, are incorporated into the shampoo formulation as discrete solid particles in suspension.

The ideal suspending agent composition homogeneously disperses the antidandruff particles throughout the composition for an indefinite period of time without affecting the viscosity, foaming, cleaning, or antidandruff properties of the shampoo. Many suspending agents operate on the principle of thickening the liquid to a great enough viscosity to retard the settling of particulate matter, having a diameter of from about 2 to about 7 microns, to such an extent that the product is stable over its lifetime. However, considering the relatively high percentage of antidandruff agent incorporated into antidandruff shampoos, a suspending agent relying only on thickening must be incorporated in such a high percentage to suspend the antidandruff agent that an unacceptably viscous product results. Shampoos having such a high viscosity are not acceptable to consumers since they are hard to dispense, hard to spread evenly on the hair and scalp, and often do not generate adequate foam.

As will become more apparent hereinafter, the suspending agent compositions of the present invention suspends a particulate antidandruff agent to an unexpectedly high degree, while maintaining viscosities suitable for hair compositions. The suspending agent compositions of the present invention are included in the shampoo in unexpectedly and unusually low levels, simplifying retention of the proper foam characteristics of the shampoo. The suspending agent compositions of the antidandruff shampoos of the present invention include a suspending alkanolamide and a wax ester, alone or in combination, in weight percentages of from about 1% to about 3% by total weight of the shampoo. As will be seen, the alkanolamides useful for particle suspension differ from the alkanolamides incorporated into the shampoo to help cleanse the hair. The suspension alkanolamides are water insoluble waxy type solids, such as stearamide MEA stearate, stearamide DEA stearate or stearamide DIBA stearate. As will become apparent, these high melting point waxy alkanolamides (generally at least about 30 carbon atoms in length) of low water solubility (less than 1% by weight) suspend particulate matter in anionic surfactant-based shampoo systems to an unexpected degree when introduced in relatively low percentages. In addition to or instead of the suspending alkanolamides, a wax ester may be used as the suspending agent. Such wax esters include, for example, stearyl stearates, myristyl myristate, myristyl stearate, cetyl myristate, cetyl stearate, ethylene glycol monostearate, ethylene glycol distearate, diethylene glycol monostearate, diethylene glycol distearate, propylene glycol monostearate, propylene glycol distearate, and propylene glycol monolaurate; however, any solid, less than 1% by weight water soluble waxy ester will serve to disperse and suspend the particulate antidandruff agent of the antidandruff shampoo compositions of the present invention. Prior to the present invention, it was impossible to provide an antidandruff shampoo having good suspension, viscosity and foaming characteristics with a suspending agent composition at a level of 4% by weight or less, of the shampoo.

It has been found that the wax esters and/or alkanolamides described above will not suspend the particulate antidandruff agent satisfactorily at the levels of 4% by weight or less for extended periods of time. However, in accordance with an important feature of the present invention, the addition of a low percentage, from about 0.1% to about 1%, of a resin containing a plurality of neutralized carboxyl groups serves to complement the wax ester and/or suspending alkanolamide to unexpectedly increase the separation stability of the antidandruff shampoo so that the level of alkanolamide and/or wax ester can be reduced to 1% to 3% by weight of the shampoo.

To achieve the full advantage of the present invention, the carboxylic acid-containing resins should be ethylene-maleic anhydride resins and/or polyacrylic acid resins. As supplied, the carboxyl-containing resins are in the acid or anhydride form and are neutralized with a suitable base such that the shampoo composition of the present invention has a pH of from about 5 to about 6.5. Generally, the degree of neutralization required to achieve a shampoo pH in the range of 5 to 6.5 is about 90% to 100% neutralization of the carboxyl groups of the resin. The resins are available in crosslinked or un-crosslinked forms, with the crosslinked resins showing the greatest utility in the shampoo composition of the present invention. The ethylene-maleic anhydride (EMA) resin or polyacrylic acid resin may be neutralized by any standard base such as the alkali metal hydroxides, ammonium hydroxide, or alkylamines containing one to four carbon atoms, to provide a neutralized, water dispersible, crosslinked resin able to aid, unexpectedly, to suspend insoluble particulate matter.

Neutralized crosslinked resins such as those used in the shampoo composition of the present invention usually lead to very rapid solution viscosity increases, even when used at very low concentrations, normally making the resins unsatisfactory for use in hair care compositions. However, quite unexpectedly, in accordance with the present invention, the combination of one or more resins having a plurality of carboxyl groups with a wax ester and/or alkanolamide does not lead to unsuitably high viscosity levels. To achieve the full advantage of the present invention, the use of low levels of a neutralized EMA or polyacrylic acid resin with low levels of a suspending alkanolamide and/or wax ester synergistically permits the total percentage of the suspension system in the composition to remain low, at a level of 4% by weight or less, thus maintaining acceptable viscosity levels while reducing the separation tendencies of the shampoo composition.

In addition to the suspending agent composition and antidandruff agent, the hair shampoo composition of the present invention includes the necessary hair cleansing ingredients including anionic surfactants; nonionic surfactants; amphoteric surfactants; a carrier, such as water; and other optional components, including but not limited to sequestering agents, preservatives, pH adjusters, fragrances, dyes and the like. No external addition of inorganic salts such as sodium chloride or ammonium chloride for viscosity enhancement is necessary. As will become apparent hereinafter, dramatic and unexpected results are obtained when a basic anionic shampoo or surfactant composition is mixed with a suspending agent composition and an antidandruff agent to provide the antidandruff hair shampoo composition of the present invention having new and unexpected efficacy and stability.

The surfactants used in the shampoo composition of the present invention are selected and blended in the proper proportions to thoroughly cleanse the hair, provide ample foaming, and to be essentially non-irritating. The major surfactant component is an anionic surfactant present in an amount from about 5% to about 20% by weight of the entire shampoo composition. The anionic surfactant performs the bulk of the cleaning of the hair and to achieve the full advantage of the present invention is selected from the sodium, ammonium, triethanolamine or monoethanolamine salt of an alkyl sulfate containing 8 to 22 carbon atoms; an alkyl ether sulfate containing 8 to 22 carbon atoms and 1 to 6 moles of ethoxylation; or a nonylphenoxypoly(ethyleneoxy) sulfate. To achieve the fullest advantage of the present invention, the anionic surfactant is ammonium lauryl sulfate.

To achieve the full advantage of the present invention, a nonionic surfactant, present in an amount of about 1% to about 10% by weight of the entire shampoo composition, is included to provide foam boosting and foam stabilization, viscosity control, and conditioning of the hair. Among the most useful nonionic surfactants are alkanolamides, including the mono- or diethanolamides of fatty acids having 8 to about 16 carbon atoms, or alkyl($C_8$—$C_{16}$) dimethyl amine oxides. To achieve the fullest advantage of the present invention, for generation of maximum foam and production of the most useful viscosity the nonionic is coconut or lauric diethanolamide. It is to be understood that an alkanolamide such as coconut diethanolamide is a liquid product that imparts detergent properties to the system as opposed to the waxy alkanolamides, such as stearamide stearate, that do not impart detergent properties to the composition, but act as suspending agents. The liquid coconut diethanolamide is a water soluble compound of the general formula (I),

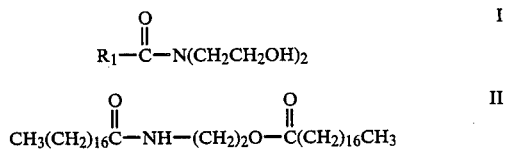

wherein $R_1$ is an alkyl group derived from coconut oil containing from about 12 to about 15 carbon atoms, whereas the waxy solid suspending alkanolamides, such as stearamide MEA stearate (Formula II), are water insoluble compounds solid at room temperature.

Detergent alkanolamides that are solids at room temperature, such as coconut monethanolamine, also may be included in the shampoo composition of the present invention. Unlike the prior art, a detergent alkanolamide may be included in the shampoo composition of the present invention as either a liquid or a solid at room temperature without adversely affecting the suspension or cleaning ability of the shampoo. As taught in the prior art, for example, in the Winkler U.S. Pat. No. 4,470,982, if the solid coconut monoethanolamide is replaced by the liquid coconut diethanolamide, shampoo separation increases greatly. In referring to FIG. 1, the Winkler U.S. Pat. No. 4,470,982 composition including coconut monoethanolamide shows slightly greater than 9% separation after 17 days at 120° F. However, replacing the solid coconut monoethanolamide with liquid coconut diethanolamide yields a composition that separates almost 17%, or almost twice as much, after 17 days at 120° F. The separation properties of the compositions of the present invention are essentially unaffected by the physical characteristics of the detergent alkanolamide, since the detergent alkanolamide does not assist in suspending solids in the shampoo compositions of the present invention.

To achieve the full advantage of the present invention, an amphoteric surfactant, at levels from about 0% to about 10% by weight of the composition, also may be incorporated into the antidandruff hair shampoo composition of the present invention, generally in combination with an anionic/nonionic surfactant blend, or as a replacement for the nonionic surfactant. The amphoteric surfactant, like the nonionic surfactant, enhances foam stability and product viscosity. To achieve the full advantage of the present invention, the amphoteric surfactant is selected from the group consisting of 8 to 18 carbon atom alkyl betaines, alkylamidopropyl betaines, alkylamidopropyl sulfobetaines and mixtures.

The surfactant blend, percentage, and ratio of surfactants are determined to provide a basic hair shampoo having excellent cleaning ability and suitable physical properties necessary for consumer acceptance. The addition of an antidandruff agent and suspending agent composition to a basic anionic hair shampoo formulation has adversely and substantially affected prior art hair shampoo formulations in that the addition of particulate matter leads to the possibility of gross product separation; the addition of suspending agents leads to unsuitable viscosity increases; and the addition of particulate matter and suspending agents generally lead to decreased foaming. The present invention materially and unexpectedly reduces these problems.

To achieve the full advantage of the present invention, it has been found that antidandruff agents can be suspended in antidandruff hair shampoos by the addition of a suspending alkanolamide and/or a wax ester plus a neutralized ethylene-maleic anhydride (EMA) resin or polyacrylic acid resin to the shampoo without adversely affecting the cleansing or physical properties of the shampoo. The addition of from about 1% to about 3.0% or less, of a wax ester and/or suspending alkanolamide and from about 0.1% to about 1.0% of a neutralized EMA or neutralized polyacrylic acid resin in a combined suspending agent composition percentage of 4.0% or less, will adequately suspend particulate antidandruff agents whereas either suspending alkanolamide and/or a wax ester alone will not adequately suspend the antidandruff agent.

To test the ability of the suspending agent composition of the present invention to suspend 2% zinc pyrithione by weight in an anionic surfactant-based hair shampoo, the shampoos of Examples 1–3 were prepared according to standard and well-known shampoo blending techniques. As seen, Example 1 contains only neutralized EMA as the suspending agent resulting in approximately 13% separation after 17 days at 120° F.; Example 2 contains only a suspending alkanolamide and a wax ester resulting in 55% separation after 17 days at 120° F.; and Example 3 contains both the neutralized EMA and suspending alkanolamide/wax ester resulting in only 4% separation after 16 days at 120° F. Previous tests showed that incorporating only 0.5% stearyl stearate wax ester as a suspending agent resulted in 97% separation after 9 days at 120° F., and that 2.0% of stearamide MEA stearate suspending alkanolamide as the only suspending agent resulted in 47% separation after 17 days at 120° F.

| INGREDIENTS | Example 1 | Example 2 | Example 3 |
| --- | --- | --- | --- |
| WATER | | qs to 100 | |
| AMMONIUM LAURYL SULFATE (anionic surfactant) | 11.25 | 11.25 | 11.25 |
| COCAMIDE DEA (detergent | 4.00 | 4.00 | 4.00 |

| INGREDIENTS | Example 1 | Example 2 | Example 3 |
|---|---|---|---|
| alkanolamide) | | | |
| ZINC PYRITHIONE (antidandruff agent) | 2.00 | 2.00 | 2.00 |
| STEARYL STEARATE (wax ester) | — | 0.50 | 0.50 |
| STEARAMIDE MEA STEARATE (suspending alkanolamide) | — | 2.00 | 2.00 |
| ETHYLENE/MALEIC ANHYDRIDE COPOLYMER (suspending resin) | 0.50 | — | 0.50 |
| AMMONIUM HYDROXIDE (EMA neutralizer) | 0.07 | — | 0.07 |
| COLOR, PERFUME, PRESERVATIVE | | qs | |

Figure 2:
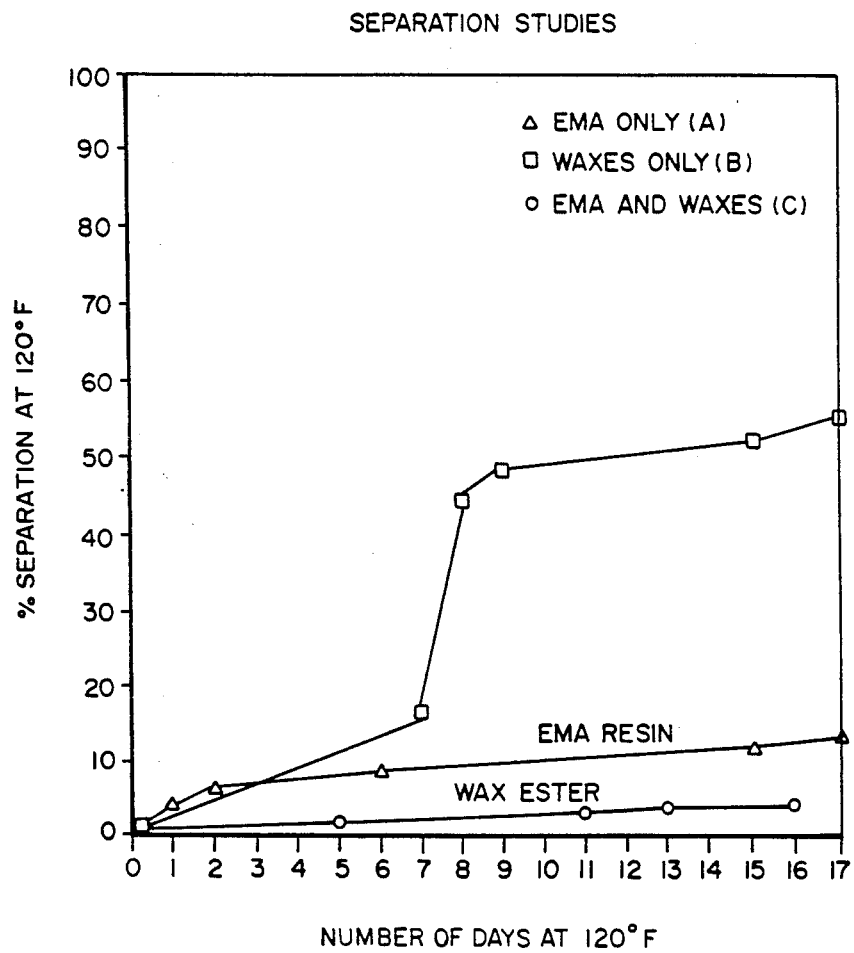
FIG. 2 is a graph comparing the ability to three suspending agent compositions: EMA alone; a suspending alkanolamide and a wax ester; and a suspending alkanolamide, a wax ester and EMA-to suspend zinc pyrithone in a hair shampoo composition.
Figure 3:
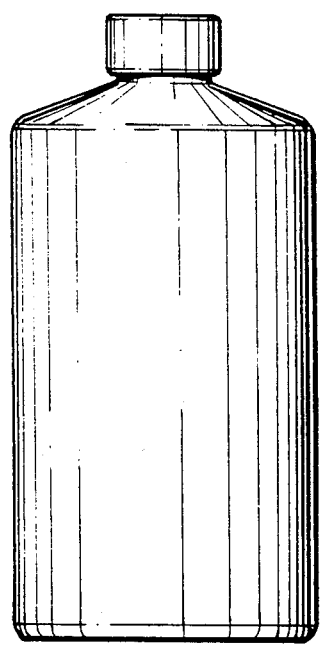
FIGS. 3 and 4 show containers used to test the antidandruff hair shampoo compositions for percent separation.
Figure 4:
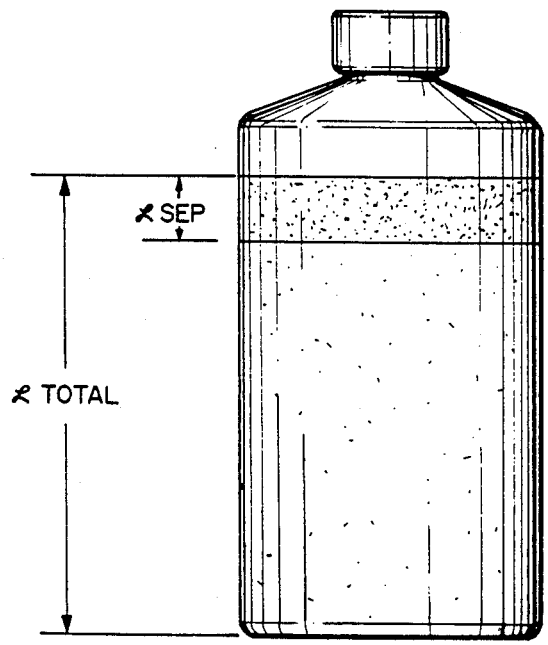

The results of a two week separation study performed at 120° F are graphed in FIG. 2. All separation studies were performed according to the following procedure. A four ounce clear, scaled container of FIG. 3 is filled approximately three quarters full with the product to be evaluated as shown in FIG. 4. A mark is placed on the scale designating the initial fill height before separation (L total), then the bottle is placed in a 120° F. oven. On each subsequent day, being careful not to disturb and to mix the liquid, the evident separation is observed and a mark is placed on the scale, designating the interface point between the two phases. After the evaluation is completed, the separation markings are measured for each day and each is recorded as L sep for that date (FIG. 4) The percentage separation is determined using the following equation:

$$\% \text{ separation} = \frac{L \text{ sep}}{L \text{ total}} \times 100\%$$

where L total is the initial fill height and L sep is the measured amount of separation.

As shown in FIG. 2, a wax ester and a suspending alkanolamide (Example 2) at a combined level of 2.5% resulted in approximately 55% separation of a 2% zinc pyrithione antidandruff hair shampoo composition after 17 days at 120° F., and 0.5% neutralized EMA resin only (Example 1) resulted in 13% separation after 17 days at 120° F. However, combining the neutralized EMA resin with the wax ester/suspending alkanolamide blend gave new and unexpected results of only 4% separation after 16 days at 120° F. In addition to reduced product separation, the antidandruff hair shampoo did not exhibit the tremendous increase in viscosity usually accompanying the use of neutralized EMA resin as a suspending agent.

In Example 4, the suspending alkanolamide, stearamide MEA stearate, has been replaced by the wax ester, ethylene glycol distearate, and the shampoo composition tested for product separation at 120° F. From the graph in FIG. 4, the composition including on ethylene glycol distearate (Example 4) exhibited only about 4% separation after 18 days at 120° F., thereby comparing favorably to the 4% separation of Example 3 after 16 days at 120° F. For comparison, a sample containing 4.0% ethylene glycol distearate as the sole suspending agent, with an addition of EMA resin, separated about 2% after 19 days at 120° F. The composition of Example 4 also possessed excellent foaming characteristics. This is a surprising result since ethylene glycol distearate is known to significantly reduce the lathering properties of even the most carefully formulated shampoos due to its inherent lipid-like characteristics.

| INGREDIENTS | EXAMPLE 4 (wt. %) |
|---|---|
| WATER | qs to 100 |
| AMMONIUM LAURYL SULFATE | 11.25 |
| COCAMIDE DEA | 4.00 |
| ZINC PYRITHIONE | 1.00 |
| STEARYL STEARATE | 0.50 |
| ETHYLENE GLYCOL DISTEARATE | 2.00 |
| ETHYLENE/MALEIC ANHYDRIDE COPOLYMER | 0.50 |
| AMMONIUM HYDROXIDE | 0.07 |
| COLOR, PERFUME, PRESERVATIVE | q.s. |

Figure 5:
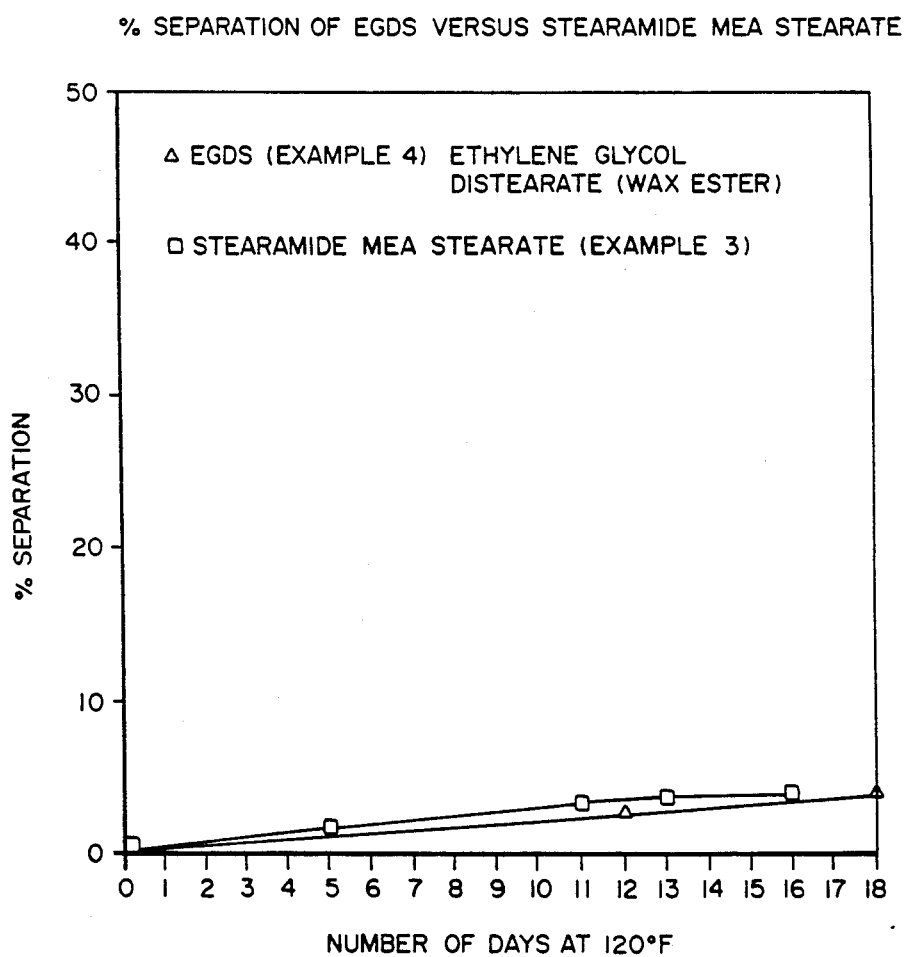
FIG. 5 is a graph comparing the ability of ethylene glycol distearate and stearamide MEA stearate to suspend zinc pyrithione in a hair shampoo composition.

In Example 5, sulfur relaced zinc pyrithione in the composition of Example 3, and the shampoo composition was tested for product separation at 120° F. FIG. 5 shows that the suspension system of the present invention also effectively suspends sulfur-based antidandruff shampoos, since the composition of Example 5 separated only 4% after 18 days at 120° F., comparing favorably with the 4% separation of the zinc pyrithione composition of Example 3.

| EXAMPLE 5 | |
|---|---|
| INGREDIENTS | % wt. |
| WATER | qs to 100 |
| ETHYLENE/MALEIC ANHYDRIDE COPOLYMER | 0.50 |
| AMMONIUM HYDROXIDE | 0.07 |
| AMMONIUM LAURYL SULFATE | 11.25 |
| COCAMIDE DEA | 4.00 |
| STEARYL STEARATE | 0.50 |
| STEARAMIDE MEA STEARATE | 2.00 |
| SULFUR | 2.03 |
| COLOR, PERFUME, PRESERVATIVE | qs |

Achieving adequate suspension of the antidandruff agent with 4% by weight or less, and generally 3% by weight or less suspending agents results in the generation of copious and stable foam. The retention of good foaming properties is important since compositions including the suspending agent composition of the present invention will have superior foaming characteristics compared to competitive antidandruff shampoos and, therefore greater consumer appeal. The retention of superior foaming qualities also allows the manufacturer the option of decreasing surfactant concentration while matching the foaming level of competitive shampoos, with subsequent economic savings; or reducing or maintaining the surfactant level for foaming purposes, but adding aesthetic ingredients, such as conditioning shampoos, to further enhance the desirability of the shampoo composition.

In accordance with the present invention, it has been found that the combined percentage of suspending alkanolamide and wax ester should be maintained at about 3% or less to avoid a rapid viscosity increase and decreased foaming properties. If the percentage of alkanolamide and wax ester rises above about 3%, the viscosity of the composition is too high and the surfactant level must be increased to regain adequate foaming. Further, at alkanolamide plus wax ester percentages above about 3.0% by weight, it has been found that neutralized EMA resins or neutralized polyacrylic acid resins do not favorably affect the viscosity or foaming characteristics of the composition. Various levels of neutralized EMA were tested to observe the overall effect on foaming, viscosity, and particulate suspension in view of the unexpectedly pronounced affect of the neutralized resin on the suspending alkanolamide/wax ester suspending agent composition of the present invention. Examples 6–10 were prepared according to the following formula by varying the neutralized EMA content from 0.1% to 0.5% by weight, in 0.1% increments.

EXAMPLES 6-10

| INGREDIENTS | % wt |
|---|---|
| WATER | qs to 100 |
| ETHYLENE/MALEIC ANHYDRIDE COPOLYMER | 0.1–0.5 |
| AMMONIUM HYDROXIDE | 0.07 |
| AMMONIUM LAURYL SULFATE | 11.25 |
| COCAMIDE DEA | 4.00 |
| STEARYL STEARATE | 0.50 |
| STEARAMIDE MEA STEARATE | 2.00 |
| ZINC PYRITHIONE | 2.00 |
| COLOR, PERFUME, PRESERVATIVE | qs |

Figure 6:
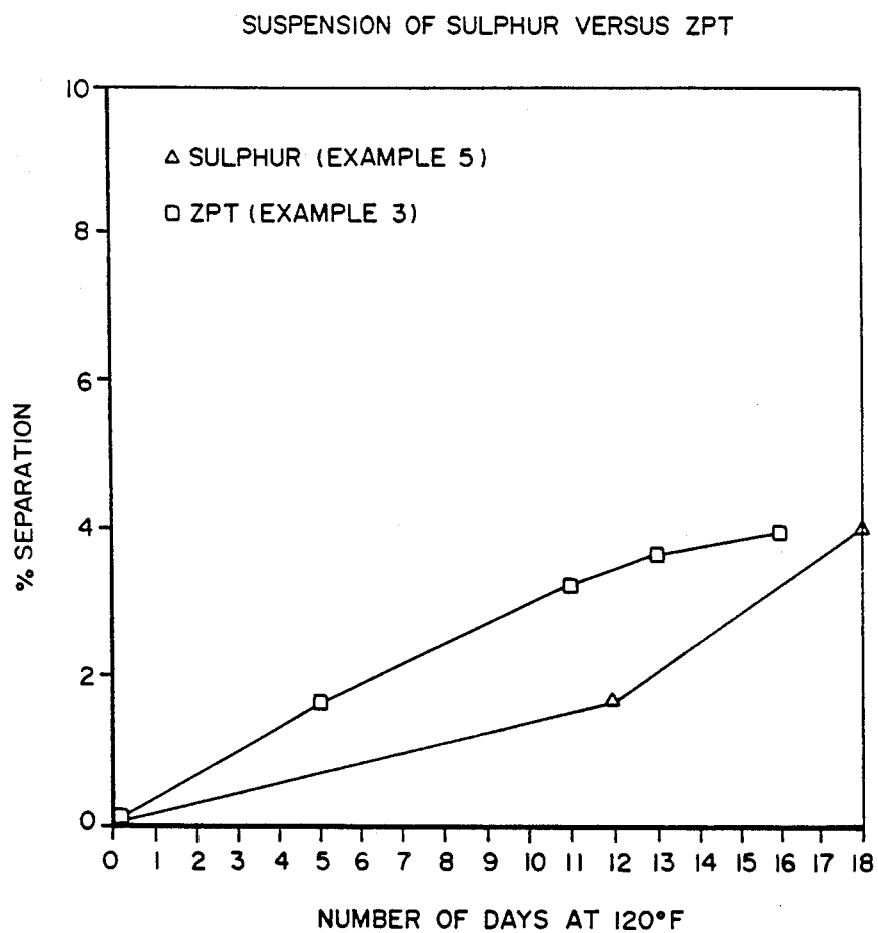
FIG. 6 is a graph comparing the ability of a suspending agent composition of the present invention to suspend sulfur and zinc pyrithione in a hair shampoo composition.

The results of the separation studies conducted at 120° F. over a 16-day period are tabulated in Table 1 and graphed in FIG. 6.

1.5% neutralized EMA is used in the composition, the Brookfield viscosity rose to an unacceptable 32,000 cps, and the shampoo began separating from the bottom indicating separation of the surfactants from the EMA. Therefore, as exemplified in Examples 6–10, FIG. 6, and other described experiments, the EMA or other neutralized polycarboxylic acid containing resin content should be from about 0.1% to about 1.0% by weight of the shampoo composition, and to achieve the full advantage of the present invention, the resin should be included in the shampoo composition in an amount between about 0.2% and about 0.5% by weight. A similar useful range is expected for the polyacrylic acid resins, since a shampoo composition including 0.5% by weight of a crosslinked polyacrylic acid resin exhibited no separation after one month at 120° F., and has essentially the same foaming and aesthetic characteristics as the EMA-containing shampoo compositions. At 0.5% weight percent neutralized resin in the composition, the foaming properties are not affected and the initial viscosity remains in the desired 2000 to 8000 cps range. Independent tests have shown that the addition of 0.5% EMA resin has less adverse affect on foaming than adding 0.5% more suspending alkanolamide/wax ester.

Separation studies also were performed on antidandruff shampoo compositions containing 0.5% neutralized EMA resin and 2.0% zinc pyrithione with varied

TABLE 1

SEPARATION EVALUATION OF VARIOUS LEVELS OF EMA

| NO. OF DAYS AT 120° F. | L SEP | | | | | % SEPARATION | | | | |
|---|---|---|---|---|---|---|---|---|---|---|
| | EX. 6 | EX. 7 | EX. 8 | EX. 9 | EX. 10 | EX. 6 | EX. 7 | EX. 8 | EX. 9 | EX. 10 |
| 1 | 1.5 | 1.3 | 0.9 | 0.7 | — | 5.36 | 4.44 | 3.10 | 2.55 | — |
| 5 | 11.0 | 2.1 | 1.2 | 1.3 | 0.5 | 39.29 | 7.17 | 4.14 | 4.74 | 1.67 |
| 8 | 12.4 | 2.5 | 1.8 | — | — | 44.29 | 8.53 | 6.21 | — | — |
| 11 | 13.7 | 3.4 | — | — | 1.0 | 48.93 | 11.6 | — | — | 3.33 |
| 12 | 14.0 | 4.0 | — | 1.5 | — | 50.00 | 13.65 | — | 5.47 | — |
| 13 | 14.2 | 4.2 | — | 1.6 | 1.1 | 50.71 | 14.33 | — | 5.84 | 3.67 |
| 16 | 15.3 | 6.3 | 2.6 | 2.0 | 1.2 | 54.64 | 21.50 | 8.97 | 7.30 | 4.00 |

| L | EX. 6 | EX. 7 | EX. 8 | EX. 9 | EX. 10 |
|---|---|---|---|---|---|
| TOTAL = | 28.0 | 29.3 | 29.0 | 27.4 | 30.0 |
| pH = | 5.76 | 5.70 | 5.53 | 5.37 | 5.26 |
| Viscosity (init) = | 710 | 1410 | 860 | 3110 | 4900 |
| Viscosity (24 hr.) = | 2790 | 3160 | 5610 | 7850 | 11,000 |
| pH (24 hr.) = | 5.87 | 5.89 | 5.68 | 5.48 | 5.31 |

From the graphs of FIG. 6, Example 6, containing 0.1% neutralized EMA, separated 55% after 16 days at 120° F., essentially the same percentage separation observed in FIG. 2 for the suspending alkanol-amide/wax ester suspension system when used alone. Dramatic and unexpected improvements in particulate suspension begin at the 0.2% EMA level (Example 7), and continue through the 0.5% EMA level (Example 10). It was observed that the improvements leveled off between 0.3% EMA and 0.5% EMA, and tests utilizing neutralized EMA at levels between 0.5% and 1.0% did not provide any sufficient further improvements in product separation over the 0.5% EMA level of Example 10. At the 1.0% EMA level, composition acceptability was marginal because the viscosity was starting to build to excessive levels and separation began to increase. At 1% neutralized EMA, the shampoo exhibited an initial Brookfield viscosity of 10,000 cps, a value in excess of the desired 2,000 cps to 8,000 cps Brookfield viscosity range. At viscosities below 2,000 cps, the shampoo composition is too watery and flows too fast and at viscosities above 8,000 cps the composition is a gel. If amounts of the suspending alkanolamide, wax ester, or combinations of alkanolamide and wax ester. Examples 11–13 were prepared by the usual techniques according to the following formulae:

| INGREDIENTS | Example 11 | Example 12 | Example 13 |
|---|---|---|---|
| WATER | qs to 100% | | |
| ETHYLENE/MALEIC ANHYDRIDE COPOLYMER | 0.50% | 0.50% | 0.50% |
| AMMONIUM HYDROXIDE | 0.07% | 0.07% | 0.07% |
| AMMONIUM LAURYL SULFATE | 11.25% | 11.25% | 11.25% |
| COCAMIDE DEA | 4.00% | 4.00% | 4.00% |
| STEARYL STEARATE | — | — | 0.50% |
| STEARAMIDE MEA STEARATE | — | 2.00% | — |
| ZINC PYRITHIONE | 2.00% | 2.00% | 2.00% |
| COLOR, PERFUME, PRESERVATIVE | qs | qs | qs |
| pH | 5.52 | 5.55 | 5.52 |
| VISCOSITY | 4080 | 5050 | 4500 |

The addition of 0.5% neutralized EMA alone (Example 11) or the addition or either 2.00% suspending alkanolamide (Example 12) or 0.50% wax ester (Example 13) leads to separation percentages ranging from about 7.1% to about 12.7% between 15 and 17 days at 120° F. (see Table 2). Comparing these separation values to the 4% separation of a system containing 0.5% neutralized EMA and 2.5% of combined suspending alkanolamide and wax ester (Example 3) shows that to achieve the full advantage of the present invention, the suspending alkanolamide and/or wax esters are present at percentages between 2.0% and 3.0% by weight of the total composition.

TABLE 2

| L TOTAL | NO. OF DAYS AT 120° F. | L SEP EX. 11 | L SEP EX. 12 | L SEP EX. 13 | % SEPARATION EX. 11 | % SEPARATION EX. 12 | % SEPARATION EX. 13 |
|---|---|---|---|---|---|---|---|
| EX. 11 = 26.0 | 1 | 1.0 | 0.7 | 1.0 | 3.85 | 2.62 | 3.21 |
| EX. 12 = 26.7 | 2 | 1.5 | — | — | 5.77 | — | — |
| EX. 13 = 31.1 | 3 | — | 1.6 | 1.2 | — | 5.99 | 3.86 |
| | 6 | 2.0 | 1.8 | 1.9 | 7.69 | 6.74 | 6.11 |
| | 8 | 2.1 | — | 2.0 | 8.08 | — | 6.43 |
| | 15 | 3.0 | 1.9 | 2.6 | 11.54 | 7.12 | 8.36 |
| | 17 | 3.3 | — | 3.2 | 12.69 | — | 10.29 |

The composition of Example 3 was compared to a commercial antidandruff hair shampoo (HEAD AND SHOULDERS) for separation stability. The composition of Example 3 contains 2% zinc pyrithione compared to the commercial product's 1.0% zinc pyrithione content, and the commercial product incorporates a different suspending agent composition at a higher percentage than the antidandruff hair shampoo of the present invention.

TABLE 3

SEPARATION STUDY FOR COMMERCIAL ANTIDANDRUFF SHAMPOO

| L TOTAL | NO. OF DAYS AT 120° F. | L SEP | % SEPARATION |
|---|---|---|---|
| 29.8 | 1 | 0.7 | 2.35 |
| | 8 | 1.0 | 3.36 |
| | 17 | 1.6 | 5.37 |

Figure 7:
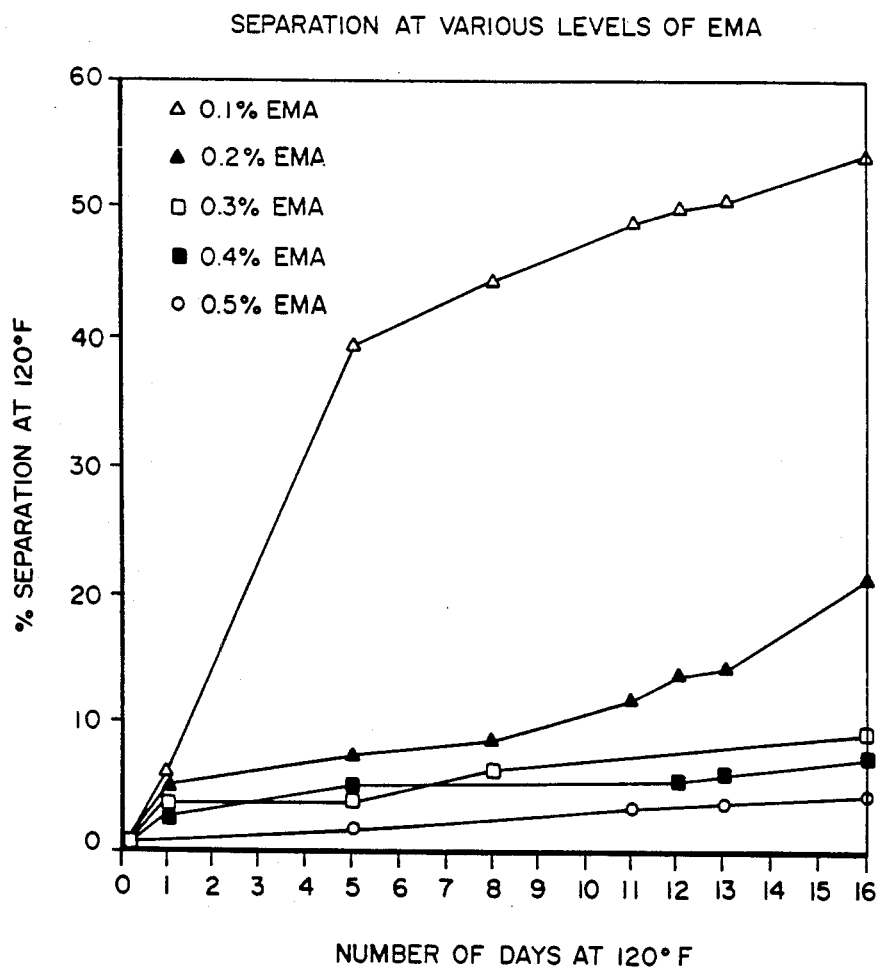
FIG. 7 is a graph comparing the ability of various percentages of EMA to suspend zinc pyrithione in a hair shampoo composition containing a fixed amount of suspending alkanolamide and wax ester.
Figure 8:
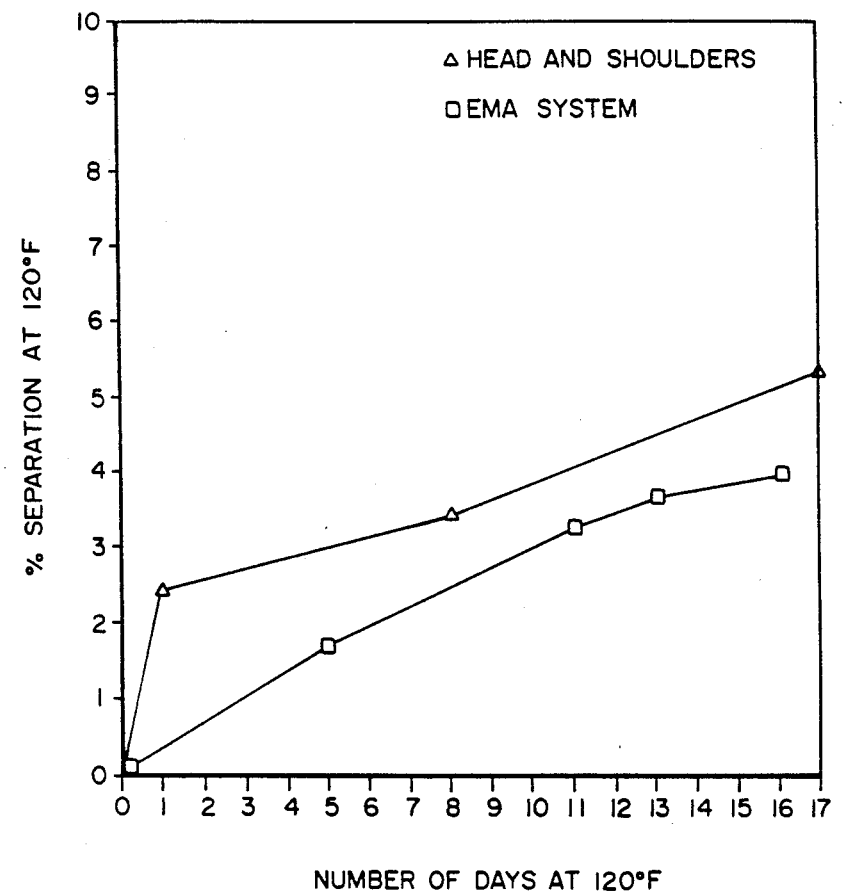
FIG. 8 is a graph comparing the suspension capability of the suspending agent composition of the present invention to a leading commercial antidandruff shampoo composition.

The data for the commercial antidandruff shampoo is listed in Table 3 and graphed in FIG. 7. As seen in FIG. 7, the shampoo of the present invention (Example 3) separates 4% after 16 days at 120° F., and the commercial product separates 5.2% after 16 days. Therefore, the composition of the present invention shows a 30% improvement in separation while maintaining suitable viscosity levels and superior foaming properties.

As an indication of these superior foaming properties, attention is directed to Examples 14–16 and Table 4.

| INGREDIENTS (wt. %) | EXAMPLE 14 | EXAMPLE 15 | EXAMPLE 16 |
|---|---|---|---|
| SOFT WATER | q.s. to 100% | | |
| EMA RESIN | 0.50 | — | 0.50 |
| AMMONIUM HYDROXIDE | 0.15 | — | 0.15 |
| AMMONIUM LAURYL SULFATE | 11.00 | 11.00 | 8.10 |
| COCAMIDE MEA | — | 3.00 | — |
| COCAMIDE DEA | 4.00 | — | 4.00 |
| GLYCOL DISTEARATE | 2.00 | 6.00 | — |
| STEARAMIDE MEA STEARATE | — | — | 2.00 |
| STEARYL STEARATE | 0.50 | — | 0.50 |
| COCAMIDOPROPYL HYDROXYSULTAINE | — | — | 1.20 |

-continued

| INGREDIENTS (wt. %) | EXAMPLE 14 | EXAMPLE 15 | EXAMPLE 16 |
|---|---|---|---|
| ZINC PYRITHIONE | 1.00 | 1.00 | 1.00 |
| COLOR, FRAGRANCE, PRESERVATIVE | | q.s. | |

TABLE 4

FOAM STUDY

| | EX. 14 vs. | EX. 15 vs. | EX. 16 |
|---|---|---|---|
| Flash foam (ml) | 800 ± 40 | 750 − 38 | 715 ± 36 |
| Final foam (ml) | 935 ± 47 | 955 ± 48 | 930 ± 47 |
| Water adhesiveness (min:sec) | 5:08 ± 0:10 | 4:30 ± 0:10 | 4:27 ± 0:10 |

Examples 14 and 16 are compositions of the present invention containing 3.0% by weight suspending agent composition, and different levels of detergent, whereas Example 15 is a prior art composition having a different suspending agent composition containing 6% by weight suspending agent. The foam studies indicate that the lower level of surfactant in Example 16 perform equally well to the prior art composition of Example 15 with respect to flash foam, final foam and water adhesiveness. In comparing the two compositions with equal surfactant levels, the foam volume figures are essentially equal; however, the water adhesiveness figures used to determine the creaminess of the lather, are significantly better for the composition of the present invention, Example 14, compared to the prior art Example 15.

The suspending agent composition of the present invention is particularly useful in suspending insoluble particulate antidandruff agents in anionic surfactant-based hair shampoo compositions. However, the suspending agent composition also may be used in other anionic surfactant systems requiring suspending agents, especially topical skin treatments such as sun screens containing zinc oxide in other solid particulate material.

What is claimed and desired to be secured by Letters Patent of the United States is:

1. An antidandruff shampoo comprising an anionic surfactant in an amount of about 5% to about 20% by weight;

a particulate antidandruff agent in an amount of about 0.2% to about 5% by weight;

a water insoluble suspending agent, solid at room temperature, selected from the group consisting of a suspending alkanolamide, a wax ester, and mixtures thereof, in an amount of about 1% to about 3% by weight;

a crosslinked ethylene maleic anhydride resin containing a plurality of neutralized carboxyl groups in an amount of about 0.3% to about 1% by weight; and a liquid carrier.

2. The antidandruff shampoo of claim 1 further comprising from about 1% to about 10% by weight of an amphoteric surfactant selected from the group consisting of alkyl betaines containing 8 to 18 carbon atoms, alkylamidopropyl betaines containing 8 to 18 carbon atoms, alkylamidopropyl sulfobetaines containing 8 to 18 carbon atoms and mixtures thereof.

3. The antidandruff shampoo of claim 1, wherein the anionic surfactant is an ammonium alkyl sulfate, sodium alkyl sulfate, triethanolamine alkyl sulfate, monoethanolamine alkyl sulfate, ammonium alkyl ether sulfate containing 3 moles of ethoxylation, ammonium nonylphenoxy(ethyleneoxy) sulfates containing 4 moles of ethoxylation or mixtures thereof.

4. The antidandruff shampoo of claim 3, wherein the anionic surfactant is ammonium lauryl sulfate or ammonium lauryl ether sulfate containing 3 moles of ethoxylation.

5. The antidandruff shampoo of claim 1 further including a nonionic surfactant in an amount of 1% to about 10% by weight.

6. The antidandruff shampoo of claim 5, wherein the nonionic surfactant is coconut diethanolamide, coconut monoethanolamide, lauric diethanloamide, lauric monoethanolamide or mixtures thereof.

7. The antidandruff shampoo of claim 1, wherein the suspending alkanolamide is stearamide MEA stearate, stearamide DEA stearate, stearamide DIBA stearate or mixtures thereof.

8. The antidandruff shampoo of claim 7, wherein the suspending alkanolamide is stearamide MEA stearate.

9. The antidandruff shampoo of claim 1, wherein the wax ester is stearyl stearate, myristyl stearate, cetyl stearate, myristyl myristate, cetyl myristate, ethylene glycol monostearate, ethylene glycol distearate, diethylene glycol distearate, propylene glycol monostearate, propylene glycol distearate or propylene glycol monolaurate.

10. The antidandruff shampoo of claim 9, wherein the wax ester is stearyl stearate, myristyl myristate, or ethylene glycol distearate.

11. The antidandruff shampoo of claim 9, wherein the wax ester is stearyl stearate or myristyl myristate.

12. The antidandruff shampoo of claim 1, wherein the suspending alkanolamide, wax ester or mixtures thereof are present in an amount of from about 1.5% to about 2.5% by weight.

13. The antidandruff shampoo of claim 1, wherein the polymer is present in an amount of about 0.5% to about 1.0% by weight.

14. The antidandruff shampoo of claim 1, wherein the crosslinked ethylene maleic anhydride resin is neutralized with an alkali metal hydroxide, ammonium hydroxide or alkyl ($C_1$ to $C_4$) amine.

15. The antidandruff shampoo of claim 1, wherein the particulate antidandruff agent is zinc pyrithione or sulfur.

16. A suspending composition for suspending particulate matter in an anionic surfactant-based liquid carrier composition comprising:

a suspending alkanolamide, wax ester or mixtures thereof in an amount of about 1% to about 3% by weight; and a crosslinked ethylene maleic anhydride polymer containing a plurality of neutralized carboxyl groups in an amount of about 0.3% to about 1% by weight.

17. The composition of claim 16, wherein the suspending alkanolamide is stearamide MEA stearate, stearamide DEA stearate, stearamide DIBA stearate or mixtures thereof.

18. The composition of claim 17, wherein the suspending alkanolamide is stearamide MEA stearate and the carrier comprises water.

19. The suspension system of claim 16, wherein the wax ester is stearyl stearate myristyl stearate, cetyl stearate, myristyl myristate, cetyl myristate, ethylene glycol distearate, propylene glycol monostearate, propylene glycol distearate or propylene glycol monolaurate.

20. The composition of claim 19, wherein the wax ester is stearyl stearate or myristyl myristate.

21. The composition of claim 16, wherein the suspending alkanolamide, wax ester or mixtures thereof are present in an amount of from about 1.5% to about 2.5% by weight.

22. The composition according to claim 16 wherein the polymer is neutralized with an alkali metal hydroxide, ammonium hydroxide or alkyl ($C_1$ to $C_4$) amine.

23. An antidandruff hair shampoo composition comprising a topically effective amount of a particulate, water insoluble antidandruff agent; a water soluble anionic sulfate detergent containing 8 to 22 carbon atoms; a water dispersible nonionic fatty acid alkanolamide containing from about 8 to about 14 carbon atoms; a crosslinked ethylene maleic anhydride resin containing a plurality of neutralized carboxyl groups in an amount of about 0.3% to about 1.0% by weight; and at least about 1.0% by weight of a water insoluble fatty acid alkanolamide or water insoluble fatty acid ester containing from about 16 to about 22 carbon atoms in a suitable carrier.

24. The composition of claim 23, wherein the composition has a pH of about 5.0 to about 6.5.

25. The composition of claim 23, wherein the anionic sulfate is present in an amount of about 5% to about 20% by weight.

26. The composition of claim 23, wherein the water dispersible fatty acid alkanolamide is present in an amount of about 1% to about 10%.

27. The composition of claim 23, wherein the crosslinked neutralized resin is a neutralized ethylene-maleic anhydride.

28. The composition of claim 23, wherein the water insoluble fatty acid alkanolamide or ester is stearyl stearate, myristyl myristate, stearamide MEA stearate, stearamide DEA stearate, ethylene glycol distearate or mixtures thereof.

29. The composition of claim 23, wherein the carrier comprises water.

30. A method of treating dandruff and cleansing human hair comprising contacting the hair with a composition comprising a topically effective amount of a particulat antidandruff agent homogeneously dispersed and suspended in a water soluble anionic sulfate detergent containing 8 to 22 carbon atoms; a cross-linked ethylene maleic anhydride resin containing a plurality of neutralized carboxyl groups in an amount of about 0.3% to about 1.0% by weight; and about 1.0% to about 3.0% by weight of a water insoluble fatty acid alkanolamide or wax ester in a suitable carrier; and thereafter rinsing the hair.

31. The method of claim 30, wherein the anionic sulfate is ammonium lauryl sulfate or ammonium lauryl ether sulfate containing 3 moles of ethoxylation and is present in an amount of about 5% to about 20% by weight.

32. The method of claim 30 wherein the resin is present from about 0.3% to about 0.6% by weight.

33. The method of claim 30, wherein the water insoluble fatty acid alkanolamide or wax ester is stearyl stearate, myristyl myristate, stearamide MEA stearate, stearamide DEA stearate or mixtures thereof, and are present in an amount of about 1.0% to about 3.0% by weight.

34. The method of claim 30, wherein the carrier comprises water.

35. An antidandruff shampoo comprising an anionic surfactant in an amount of about 5% to about 20% by weight;
a particulate antidandruff agent in an amount of about 0.2% to about 5% by weight;
a water insoluble suspending agent, solid at room temperature, selected from the group consisting of a suspending alkanolamide, a wax ester, and mixtures thereof, in an amount of about 1% to about 3% by weight;
a cross-linked ethylene maleic anhydride resin in an amount of about 0.6% to about 1% by weight; and
a liquid carrier.

36. An antidandruff shampoo comprising an anionic surfactant in an amount of about 5% to about 20% by weight;
a particulate antidandruff agent in an amount of about 0.2% to about 5% by weight;
a water insoluble suspending agent, solid at room temperature, selected from the group consisting of a suspending alkanolamide, a wax ester, and mixtures thereof, in an amount of about 1% to about 3% by weight;
a cross-linked ethylene maleic anhydride resin in an amount of about 0.3% to about 1% by weight; and
a liquid carrier.

37. An antidandruff shampoo comprising an anionic surfactant in an amount of about 5% to about 20% by weight;
a particulate antidandruff agent in an amount of about 0.2% to about 5% by weight;
a water insoluble suspending alkanolamide, solid at room temperature, in an amount of about 1% to about 3% by weight;
a crosslinked ethylene maleic anhydride resin containing a plurality of neutralized carboxyl groups in an amount of about 0.3% to about 1% by weight; and
a liquid carrier.

38. An antidandruff shampoo comprising an anionic surfactant in an amount of about 5% to about 20% by weight;
a particulate antidandruff agent in an amount of about 0.2% to about 5% by weight;
a water insoluble suspending wax ester, solid at room temperature, in an amount of about 1% to about 3% by weight;
a crosslinked ethylene maleic anhydride resin containing a plurality of neutralized carboxyl groups in an amount of about 0.3% to about 1% by weight; and
a liquid carrier.

39. The antidandruff shampoo of claim 38, wherein the wax ester is selected from the group consisting of ethylene glycol monostearate, ethylene glycol distearate, diethylene glycol distearate, propylene glycol monostearate, propylene glycol distearate or propylene glycol monolaurate.

40. An antidandruff hair shampoo composition comprising a topically effective amount of a particulate, water insoluble antidandruff agent; a water soluble anionic sulfate detergent containing 8 to 22 carbon atoms; a water dispersible nonionic fatty acid alkanolamide containing from about 8 to about 14 carbon atoms; a crosslinked ethylene maleic anhydride resin containing a plurality of neutralized carboxyl groups in an amount of about 0.3% to about 1.0% by weight; and a water insoluble fatty acid ester in an amount of at least about 1% by weight in a suitable carrier.

41. The antidandruff hair shampoo of claim 40 wherein the fatty acid of the water insoluble fatty acid ester is lauric acid or stearic acid.

42. The antidandruff hair shampoo of claim 40 wherein the glycol of the ester is ethylene glycol or propylene glycol.

43. The antidandruff hair shampoo of claim 40 wherein the water insoluble fatty acid ester or is selected from the group consisting of ethylene glycol monostearate, ethylene glycol distearate, propylene glycol distearate and propylene glycol monolaurate; or mixtures thereof.

44. A method of treating dandruff and cleansing human hair comprising contacting the hair with a composition comprising a topically effective amount of a particulate antidandruff agent homogeneously dispersed and suspended in a water soluble anionic sulfate detergent containing 8 to 22 carbon atoms; a crosslinked ethylene maleic anhydride resin containing a plurality of neutralized carboxyl groups in an amount of about 0.3% to about 1.0% by weight; and a water insoluble fatty acid wax ester in an amount of at least about 1% by weight in a suitable carrier; and thereafter rinsing the hair.

45. The method of claim 44 wherein the fatty acid of the wax ester is lauric acid or stearic acid.

46. The method of claim 44 wherein the glycol of the ester is ethylene glycol or propylene glycol.

47. The method of claim 44 wherein the wax ester is selected from the group consisting of ethylene glycol monostearate, ethylene glycol distearate, propylene glycol distearate and propylene glycol monolaurate; or mixtures thereof.

* * * * *